(12) United States Patent
Kobayashi et al.

(10) Patent No.: US 11,707,063 B2
(45) Date of Patent: *Jul. 25, 2023

(54) COMPOUND, PRODUCTION METHOD THEREFOR, AND HYDROGEN SUPPLY METHOD

(71) Applicants: BOSQUET SILICON CORP., Osaka (JP); KIT Co., Ltd., Osaka (JP)

(72) Inventors: Hikaru Kobayashi, Kyoto (JP); Yuki Kobayashi, Kyoto (JP)

(73) Assignees: BOSQUET SILICON CORP., Osaka (JP); KIT Co., Ltd., Osaka (JP)

(*) Notice: Subject to any disclaimer, the term of this patent is extended or adjusted under 35 U.S.C. 154(b) by 22 days.

This patent is subject to a terminal disclaimer.

(21) Appl. No.: 16/327,782

(22) PCT Filed: Jul. 27, 2017

(86) PCT No.: PCT/JP2017/027174
§ 371 (c)(1),
(2) Date: Feb. 22, 2019

(87) PCT Pub. No.: WO2018/037819
PCT Pub. Date: Mar. 1, 2018

(65) Prior Publication Data
US 2019/0216082 A1 Jul. 18, 2019

(30) Foreign Application Priority Data
Aug. 23, 2016 (JP) .................................. 2016-162520

(51) Int. Cl.
C01B 33/02 (2006.01)
C01B 3/06 (2006.01)
C05G 3/00 (2020.01)
A01N 25/12 (2006.01)
C02F 1/68 (2023.01)
A01N 59/00 (2006.01)

(52) U.S. Cl.
CPC ............ *A01N 25/12* (2013.01); *A01N 59/00* (2013.01); *C01B 3/06* (2013.01); *C01B 33/02* (2013.01); *C02F 1/68* (2013.01); *C05G 3/00* (2013.01); *C01P 2004/50* (2013.01); *C01P 2004/64* (2013.01)

(58) Field of Classification Search
CPC .......... A01N 25/12; A01N 59/00; C01B 3/06; C01B 33/02; C02F 1/68; C05G 3/00; C01P 2004/50; C01P 2004/64
See application file for complete search history.

(56) References Cited

U.S. PATENT DOCUMENTS

| 10,617,712 B2 | 4/2020 | Kobayashi et al. |
| 10,617,782 B2 | 4/2020 | Zhang et al. |
| 11,311,572 B2 | 4/2022 | Kobayashi et al. |
| 2003/0033991 A1 | 2/2003 | Cheng |
| 2003/0059361 A1 | 3/2003 | Carberry |
| 2004/0067247 A1* | 4/2004 | De Sloovere ........ A01N 25/04 424/409 |
| 2005/0232837 A1 | 10/2005 | Troczynski et al. |
| 2009/0175985 A1 | 7/2009 | Canham |
| 2011/0311633 A1 | 12/2011 | Canham et al. |
| 2012/0034147 A1 | 2/2012 | Okita |
| 2012/0275981 A1* | 11/2012 | Foord ................... C01B 3/065 423/274 |
| 2012/0315684 A1 | 12/2012 | Hayashi et al. |
| 2013/0098250 A1 | 4/2013 | Satoh et al. |
| 2014/0377176 A1 | 12/2014 | Stephan et al. |
| 2015/0258136 A1 | 9/2015 | Lucas |
| 2016/0200571 A1 | 7/2016 | Kobayashi et al. |
| 2017/0333518 A1 | 11/2017 | Uekita et al. |
| 2019/0038664 A1 | 2/2019 | Kobayashi et al. |
| 2019/0231660 A1 | 8/2019 | Kobayashi et al. |
| 2020/0067554 A1 | 2/2020 | Kobayashi et al. |

FOREIGN PATENT DOCUMENTS

| CN | 102227375 A | 10/2011 |
| CN | 102741172 A | 10/2012 |
| EP | 1220659 B1 | 9/2004 |
| EP | 1452484 A1 | 9/2004 |
| EP | 2630944 A1 | 8/2013 |
| JP | H0466189 U | 3/1992 |
| JP | 2004115349 A | 4/2004 |
| JP | 2006071330 A | 3/2006 |
| JP | 2006083078 A | 3/2006 |

(Continued)

OTHER PUBLICATIONS

Erogbogbo et al. (Nano Lett. 2013, 13, 451-456). (Year: 2013).*
Medical Definition of Quasi (obtained online via www.medicinenet.com) (Year: 2021).*
Bases—pH Values (obtained online via www.engineeringtoolbox.com) (Year: 2021).*
English translation of Office Action for TW Application No. 106125642, dated Jan. 5, 2021.
"Mainly" Merriam-Webster.com. 2019. http://merriam-webster.com (Aug. 6, 2019).
English Translation of Notice of Reasons for Refusal received in JP Application No. 2018-535547 dated Jul. 9, 2019.

(Continued)

*Primary Examiner* — Patricia Duffy
*Assistant Examiner* — Garen Gotfredson
(74) *Attorney, Agent, or Firm* — Dorsey & Whitney LLP

(57) ABSTRACT

One compound (100) according to the present invention contains silicon fine particles having a capability of generating hydrogen or aggregates of the silicon fine particles. The compound that contains the silicon fine particles or the aggregates having a capability of generating hydrogen is capable of generating hydrogen in the body of, for example, an animal that has ingested the compound. For a plant, the compound can be disposed or charged into, for example, moisture (water-containing liquid) or fertilizer to be provided to the plant, to supply the plant with hydrogen generated from the compound.

13 Claims, 8 Drawing Sheets

(56) References Cited

FOREIGN PATENT DOCUMENTS

| | | | | |
|---|---|---|---|---|
| JP | 2007521244 A | 8/2007 | | |
| JP | 2007523096 A | 8/2007 | | |
| JP | 2008019115 A | 1/2008 | | |
| JP | 2008036530 A | 2/2008 | | |
| JP | 2008247839 A | 10/2008 | | |
| JP | 2009502157 A | 1/2009 | | |
| JP | 2009503128 A | 1/2009 | | |
| JP | 2010045204 A | 2/2010 | | |
| JP | 2010265158 A | 11/2010 | | |
| JP | 2011026211 A | 2/2011 | | |
| JP | 2011506279 A | 3/2011 | | |
| JP | 2011218340 A | 11/2011 | | |
| JP | 2011251873 A | 12/2011 | | |
| JP | 2013199413 A | 10/2013 | | |
| JP | 2013228319 A | 11/2013 | | |
| JP | 2014019689 A | 2/2014 | | |
| JP | 5514140 B2 | 4/2014 | | |
| JP | 2014084233 A | 5/2014 | | |
| JP | 2014193792 A | 10/2014 | | |
| JP | 2014205635 A | 10/2014 | | |
| JP | 2014227346 A | 12/2014 | | |
| JP | 2015113331 A | 6/2015 | | |
| JP | 2015531363 A | 11/2015 | | |
| JP | 2016001613 A | 1/2016 | | |
| JP | 2016152796 A | 8/2016 | | |
| JP | 2016155118 A | 9/2016 | | |
| JP | 2017104848 A | 6/2017 | | |
| JP | 6508664 B1 | 4/2019 | | |
| JP | 6592725 B2 | 10/2019 | | |
| KR | 10-1318939 | 10/2013 | | |
| KR | 101318939 B1 | 11/2013 | | |
| TW | I295935 B | 4/2008 | | |
| TW | 201126592 A | 8/2011 | | |
| TW | 201518206 A | 5/2015 | | |
| WO | 2005046707 A1 | 5/2005 | | |
| WO | 2005097670 A1 | 10/2005 | | |
| WO | 2009071219 A2 | 6/2009 | | |
| WO | 2010038064 A1 | 4/2010 | | |
| WO | 2012053472 A1 | 4/2012 | | |
| WO | 2014049677 A1 | 4/2014 | | |
| WO | 2015033815 A1 | 3/2015 | | |
| WO | WO-2015033815 A1 * | 3/2015 | ................ | B01J 7/02 |
| WO | WO2015033815 A1 * | 3/2015 | ............... | C01B 3/06 |
| WO | 2016010139 A1 | 1/2016 | | |
| WO | 2016129512 A1 | 8/2016 | | |
| WO | 2007026533 A1 | 3/2017 | | |
| WO | 2017130709 A1 | 8/2017 | | |

OTHER PUBLICATIONS

Bourzac, Katherine, "Hydrogen Fuel on Demand with Silicon Nanoparticles," Chemical & Engineering News (Jan. 24, 2013) https://cen.acs.org/content/cen/articles/91/web/2013/01/Hydrogen-Fuel-Demand-Silicon-Nanoparticles.html.
Loyless, Clay J. et al., "A Sodium Bicarbonate Dosing Methodology for pH Management in Freshwater-Recirculating Aquaculture Systems" 59 the Progressive Fish-Culturist 198-205 (1997).
Machine translation of WO/2015033815 A1, obtained Apr. 26, 2020.
Machine translation of WO/2016010139, obtained Apr. 26, 2020.
English translation of Office Action for IN Application No. 201927007362, dated Nov. 17, 2020.
English translation of Office Action for IN Application No. 201927007363, dated Oct. 28, 2020.
English translation of Office Action for TW Application No. 106102324, dated Nov. 12, 2020.
English Translatlon of Shinsuke Matsude, "Concentration of hydrogen molecules and splitting water using silicon nanoparticle," ISIR Osaka Univ., 2015.
Kentaro Imamura, et al, "Hydrogen generation from water using Si nanopower fabricated from swart", Journal of Nanoparticle Research, vol. 18, No. 5, 2016.
English Translation of Notification of Reasons for Refusal received in JP Application No. 2019-131994 dated Aug. 13, 2019.
Extended European Search Report received in EP App. No. 17843304.1 dated Feb. 7, 2020.
Extended European Search Report received in EP App. No. 17843305.8 dated Feb. 7, 2020.
Extended European Search Report for EP Application No. 17743940.3, dated Jul. 26, 2019.
Non-Final office action received in U.S. Appl. No. 16/073,305 dated Aug. 12, 2019.
English translation for Office Action for JP Application No. 2019-034384, dated Dec. 15, 2020.
English translation of Office Action for IN Application No. 201927007366, dated Dec. 10, 2020.
Office Action for EP Application No. 17743940.3, dated Jan. 12, 2021.
Canham, L T., "Nanoscale Semiconducting Silicon as a Nutritional Food Additive", Nanotechnology, vol. 18, No. 18, Apr. 2007.
Shabir, Qurrat et al., "Taste and Mouthfeel Assessment of Porour and Non-Porous Silicon Microparticles", Nanoscale Research Letters, vol. 7, No. 1, Jul. 20, 2012, pp. 1-6.
English translation of CN Office Action for Application No. 201780008361.2, dated Apr. 26, 2020.
English translation of IN Office Action for Application No. 201827031149, dated Mar. 20, 2020.
English translation for Office Action for TW Application No. 106125643, dated Oct. 6, 2020.
English translation of Office Action for TW Application No. 106125642, dated Oct. 7, 2020.
Erogbogbo, Folarin et al., "On-Demand Hydrogen Generation Using Nanosilicon: Splitting Water Without Light, Heat, or Electricity", Nano Letters, vol. 13, published Jan. 14, 2013, pp. 451-456.
English Translation for Office Action dated Feb. 26, 2019 for Japanese application No. 2018-229323.
English Translation of Office Action dated Dec. 4, 2018 for Japanese application No. 2017-563788.
English Translation of Office Action dated Nov. 26, 2018 for Japanese application No. 2017-563788.
Matsuda, et al., "Concentration of Hydrogen Molecules and Splitting Water Using Silicon Nanoparticle", The 62nd JSAP Spring Meeting Koen Yokoshu, Mar. 2015.
English translation of Office Action for CN Application No. 201780008361.2, dated Sep. 27, 2020.
English translation of Office Action for TW Application No. 106125644, dated Oct. 6, 2020.
English translation of Notice of Reasons for Refusal for JP Application No. 2017-135940, dated Jul. 14, 2020.
English Translation of Brazilian Office Action dated Sep. 21, 2021 for Brazilian Application No. 112018015391-5.
English Translation of Japanese Office Action dated Aug. 24, 2021 for Japanese Application No. 2021-063404.
English Translation of Japanese Office Action dated Sep. 14, 2021 for Japanese Application No. 2019-034384.
English Translation of Taiwanese Office Action dated Aug. 3, 2021 for Taiwanese Application No. 109140194.
English Translation of Taiwanese Office Action dated Aug. 3, 2021 for Taiwanese Application No. 109140195.
English Translation of Taiwanese Office Action dated Aug. 4, 2021 for Taiwanese Application No. 110102396.
English Translation of Taiwanese Second Office Action dated Oct. 4, 2021 for Taiwanese Application No. 109140195.
English machine translation of PCT Publication No. WO 2017130709 (obtained Jun. 2021).
English Translatlon for Office Action for JP Application No. 2019-181958, dated Jun. 2, 2021.
English translation of Hearing Notice for Indian Application No. 201827031149, mailed Jun. 4, 2021.
English translation of Hearing Notice for Indian Application No. 201927007366, mailed May 19, 2021.
English translation of Office Action for Chinese Application No. 201780051862.9, dated May 21, 2021.
English Translation of Office Action for Japanese Application No. 2018-535516, dated on May 25, 2021.

(56) References Cited

OTHER PUBLICATIONS

English translation of Office Action for Japanese Application No. 2018-535548, dated Jun. 1, 2021.
English translation of Office Action for JR Application No. 2019-181957, dated Jun. 2, 2021.
[English Translation] Final Notification of Reasons for Refusal dated Nov. 30, 2021 for Japanese Application No. 2021-063404.
[English Translation] Notification of Written Opinion on the First Examination dated Oct. 15, 2021 for Chinese Application No. 201780052364.4.
[English Translation] Notification of Written Opinion on the Second Examination dated Oct. 18, 2021 for Chinese Application No. 201780051862.9.
Non-Final Rejection received in U.S. Appl. No. 16/327,794 dated Jan. 5, 2022.
[English Translation] 2nd Office Action dated Mar. 29, 2022 for Chinese Patent Application No. 201780052364.4; pp. all.
[English Translation] Notice of Reasons for Refusal dated Jun. 7, 2022 for Japanese Patent Application No. 2021-066958; pp. all.
[English Translation] Notice of Reasons for Refusal dated Aug. 2, 2022 for Japanese Patent Application No. 2021-101920; pp. all.
[English Translation] The First Office Action dated Jul. 27, 2022 for Chinese Patent Application No. 202110564197.1; pp. all.
The Examination Report dated Aug. 22, 2022 for Indian Patent Application No. 202128007875; pp. all.
The Examination report dated Aug. 29, 2022 for Indian Patent Application No. 202128037822; pp. all.
The Examination report dated Aug. 29, 2022 for Indian Patent Application No. 202128037824; pp. all.
[English Translation] Chinese Office Action dated Mar. 11, 2022 for Chinese Patent Application No. 201780051862.9; pp. all.
[English Translation] Chinese Office Action dated Mar. 3, 2022 for Chinese Patent Application No. 201780051870.3; pp. all.
[English Translation] Final Notice of Reasons for Refusal dated Mar. 8, 2022 for Japanese Patent Application No. 2019-181958; pp. all.
[English Translation] Final Notification of Reasons for Refusal dated Feb. 15, 2022 for Japanese Patent Application No. 2018-535516; pp. all.
[English Translation] Taiwanese Office Action dated Jan. 6, 2022 for Taiwanese Patent Application No. 110104778; pp. all.
[English Translation] Taiwanese Office Action dated Jan. 17, 2022 for Taiwanese Patent Application No. 109140194; pp. all.
[English Translation] Taiwanese Office Action dated Jan. 17, 2022 for Taiwanese Patent Application No. 109140195; pp. all.
[English Translation] Taiwanese Office Action dated Jan. 17, 2022 for Taiwanese Patent Application No. 110131758; pp. all.
Hearing Notice dated Jan. 21, 2022 for Indian Patent Application No. 201927007362; pp. all.
Continuation U.S. Appl. No. 17/679,973 titled "Solid Preparation, Method for Producing Solid Preparation, and Method for Generating Hydrogen" filed Feb. 24, 2022; pp. all pages of application as filed.
[English Translation] Taiwanese Office Action for Taiwanese Patent Application No. 111110405 dated Dec. 13, 2022, pp. all.
[English Abstract] Cheng, Ya-Yi, "Preparation and Characterization of Si and FeSi Nanoparticles", NCKU Institutional Repository; Item 987654321/92947; [Department of Chemical Engineering] Dissertations and Theses, pp. all, Jun. 2009, 11 pages.
The Hearing Notice mailed on Dec. 13, 2022 for Indian Patent Application No. 201927007363, pp. all.
[English Translation] First Office Action for Chinese Patent Application No. 202110806702.9 dated Oct. 10, 2022, pp. all.
[English Translation] Notice of Reasons for Refusal for Japanese Patent Application No. 2021-182376 dated Oct. 24, 2022, pp. all.
[English Translation] Second Office Action for Chinese Patent Application No. 201780051870.3 dated Sep. 15, 2022, pp. all.
[English Translation] Second Office Action for Chinese Patent Application No. 202110564197.1 dated Oct. 12, 2022, pp. all.
Communication Pursuant to Article 94(3) EPC for European Patent Application No. 17843305.8 dated Nov. 3, 2022, pp. all.
European Office Action for European Patent Application No. 17843304.1 dated Nov. 3, 2022, pp. all.
The Examination Report for Indian Patent Application No. 202128034241 dated Oct. 18, 2022, pp. all.
[English Translation] Notification of Written Opinion on the Third Examination for Chinese Patent Application No. 201780051870.3 dated Feb. 24, 2023, pp. all.
Hearing Notice in Reference of Indian Patent Application No. 202128037822 dated Mar. 29, 2023, pp. all.
Hearing Notice in Reference of Indian Patent Application No. 202128037824 dated Mar. 30, 2023, pp. all.
[English Translation] Notice of Reasons for Refusal for Japanese Patent Application No. 2022-051528 dated Jan. 27, 2023, pp. all.
[English Translation] Notification of Written Opinion on the Third Examination for Chinese Patent Application No. 202110564197.1, dated Feb. 21, 2023, pp. all.
[English Translation] Taiwanese Office Action for Taiwanese Patent Application No. 111110407 dated Jan. 12, 2023, pp. all.
[English Translation] Taiwanese Office Action for Taiwanese Patent Application No. 111110408 dated Jan. 12, 2023, pp. all.
Canadian Office Action for Canadian Patent Application No. 3,048,952 dated Jan. 31, 2023, pp. all.
Hearing Notice in Reference of Indian Application No. 202128034241 dated May 4, 2023, pp. all.

* cited by examiner

[Fig.1]
(a)
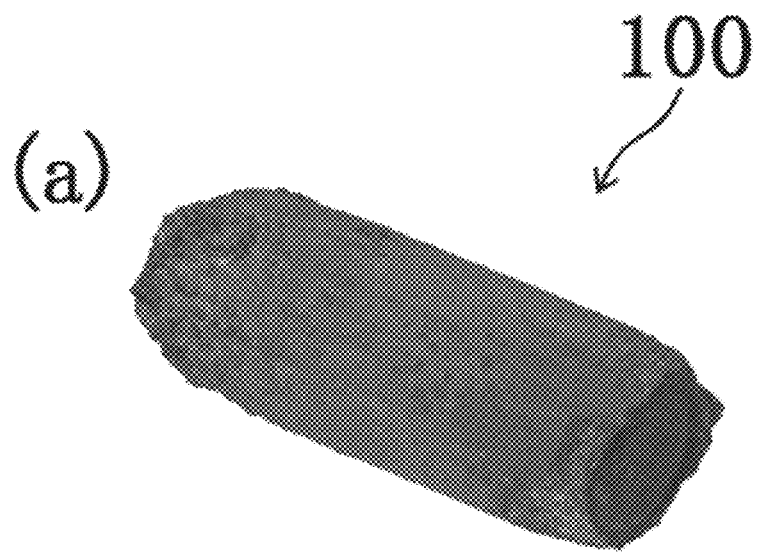
100
(b)
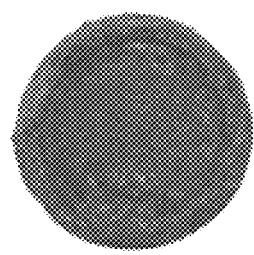

[Fig.2]
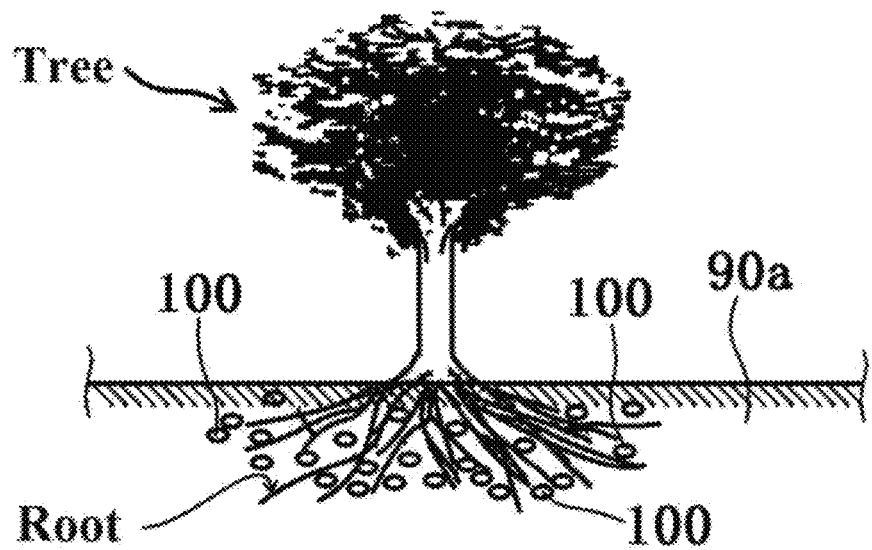
[Fig.3A]
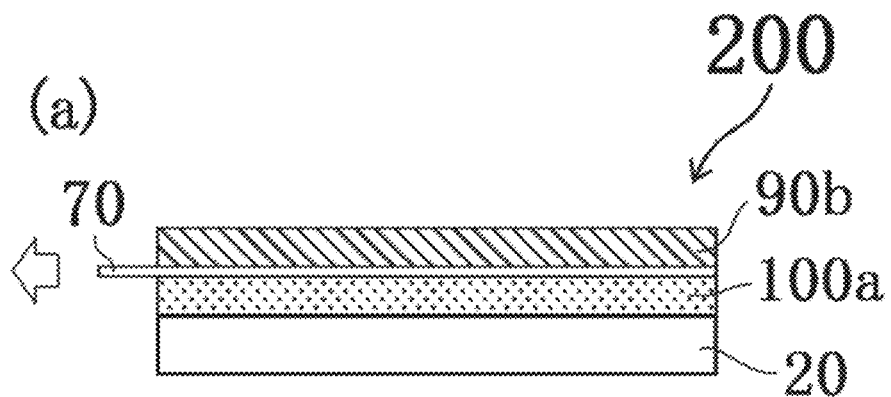
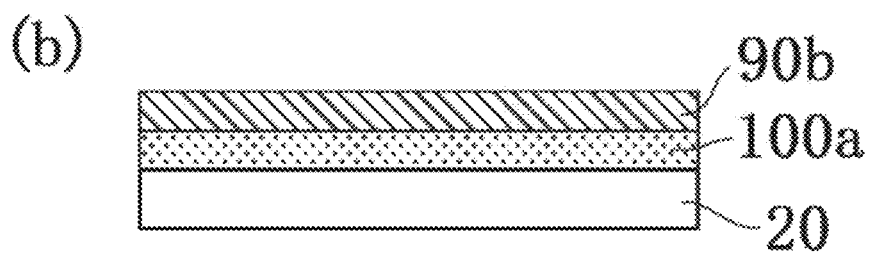

[Fig.3B]
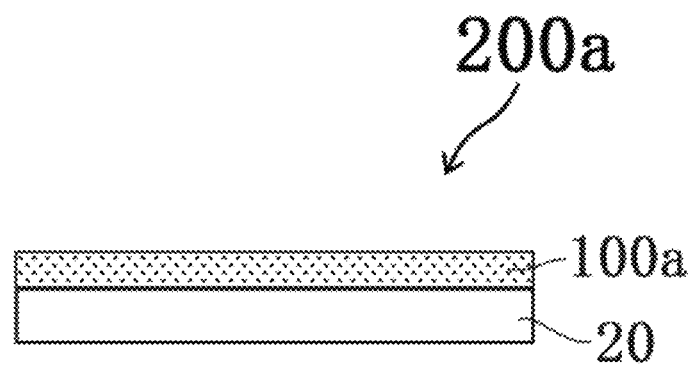
[Fig.4]
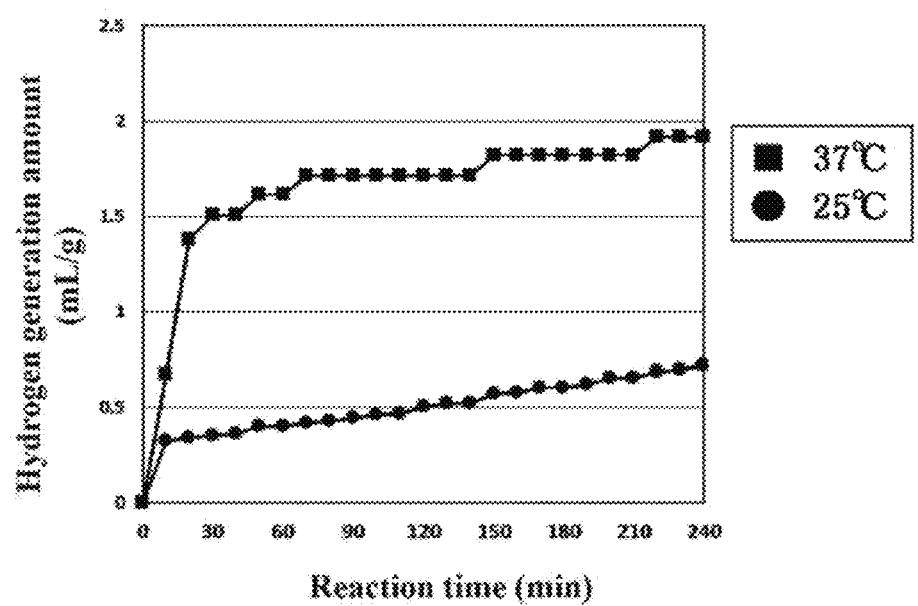

[Fig.5A]

[Fig.5B]
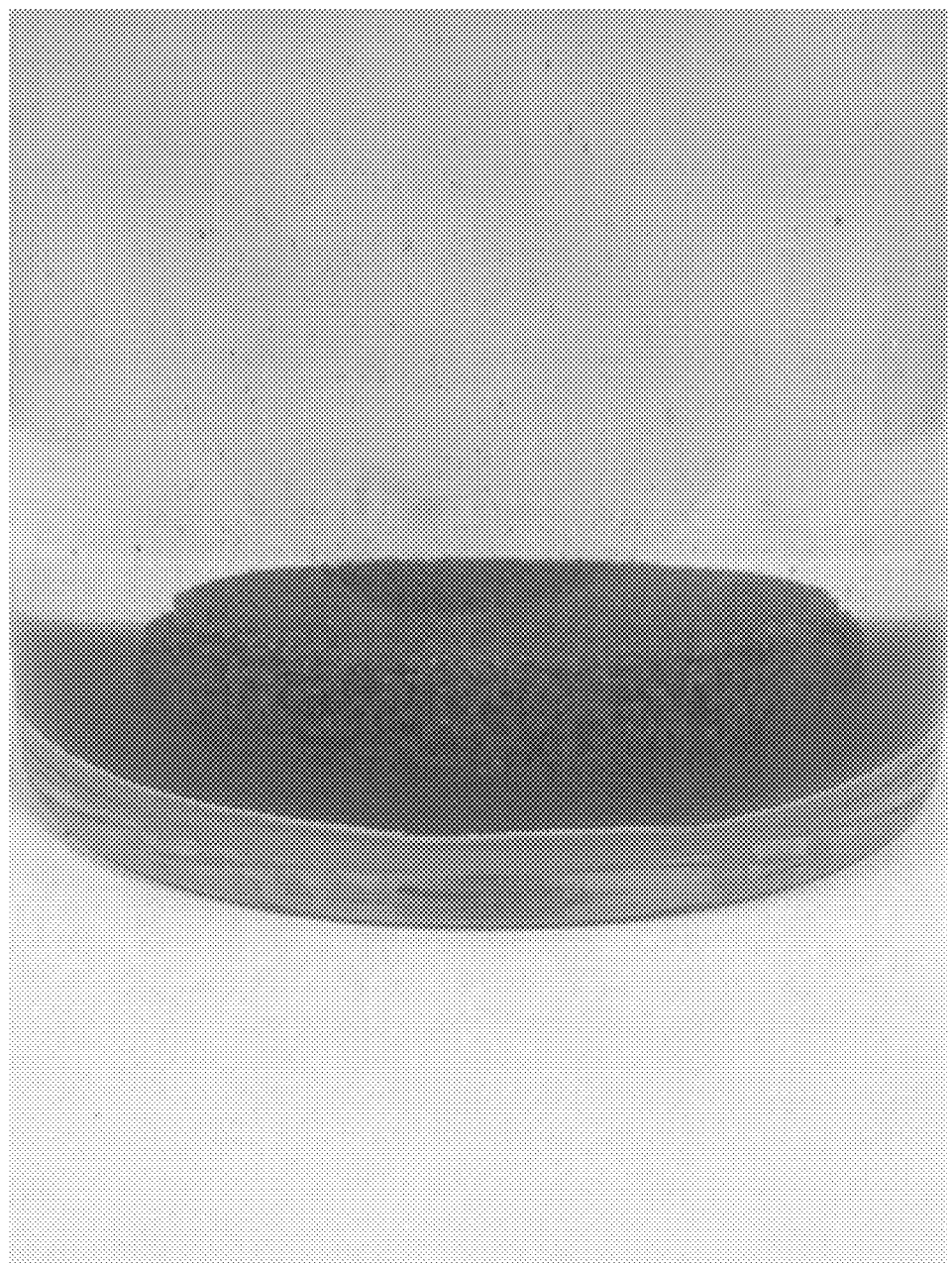

[Fig.5C]
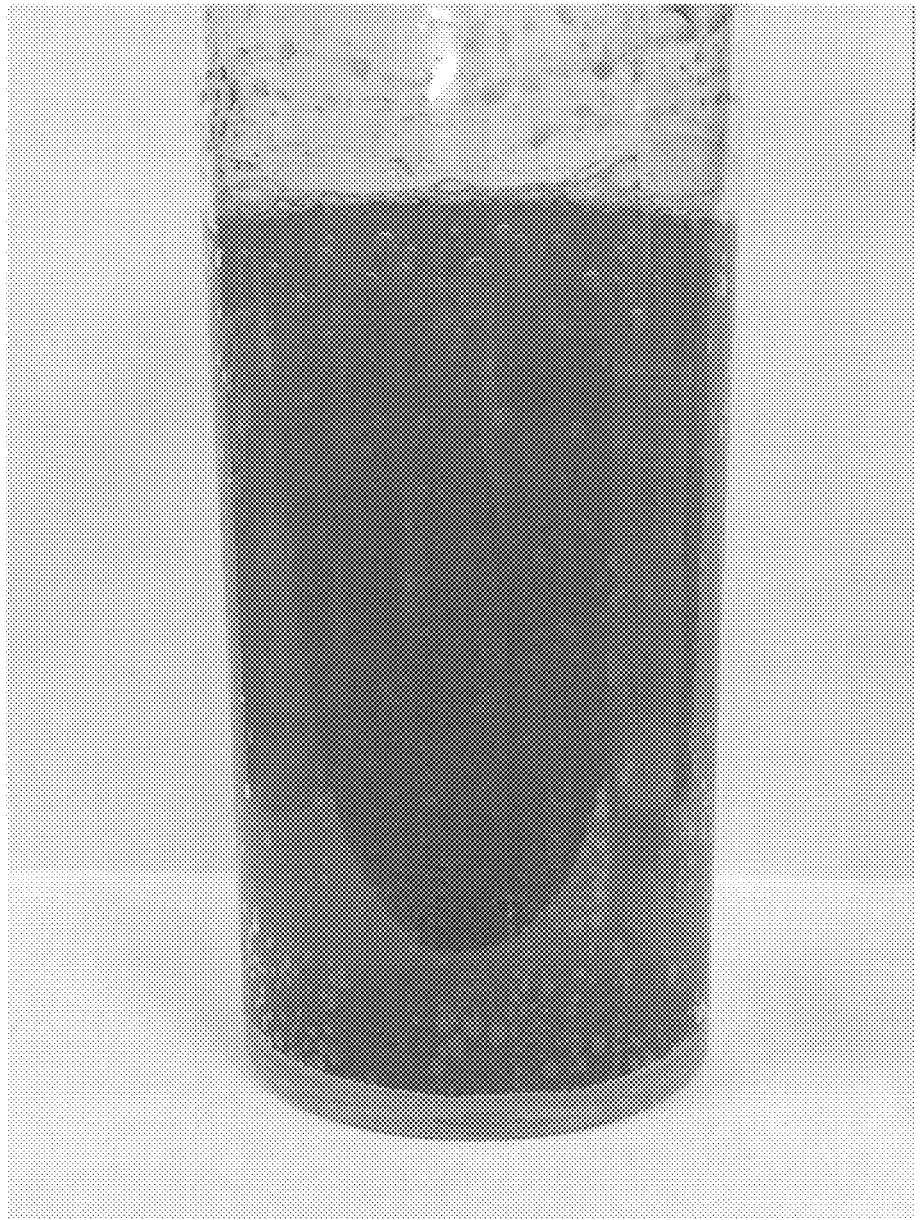

[Fig.6]
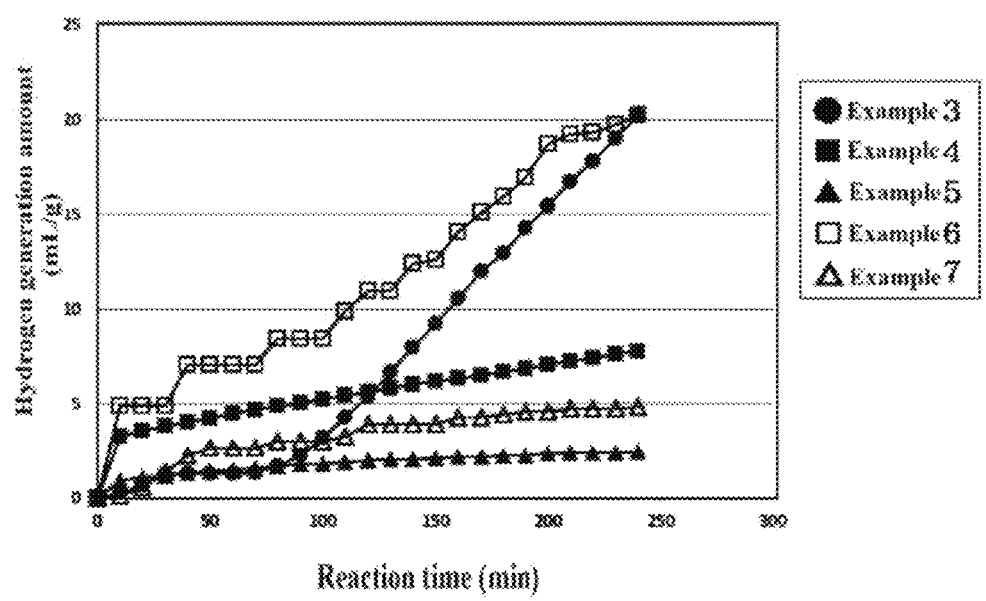

[Fig. 7]
(a)
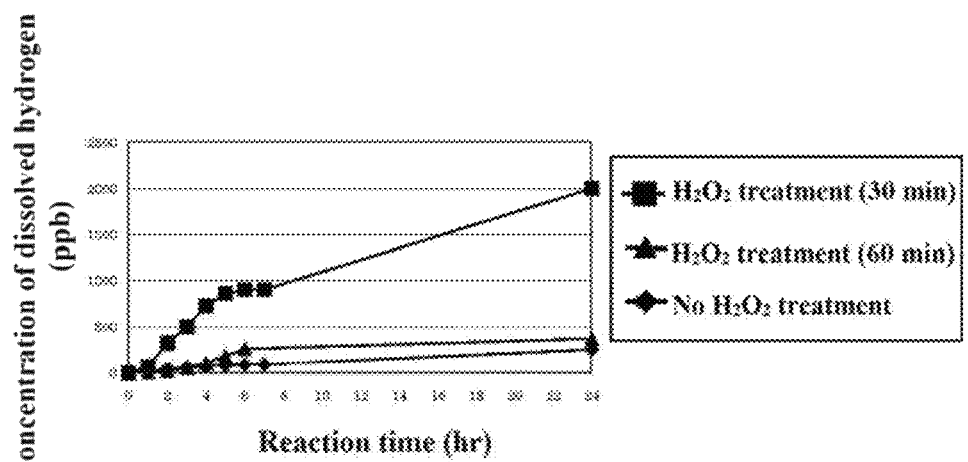
(b)
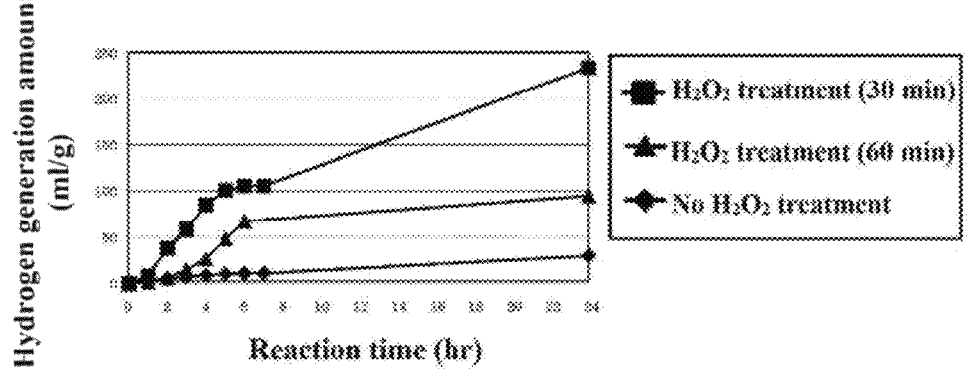

COMPOUND, PRODUCTION METHOD THEREFOR, AND HYDROGEN SUPPLY METHOD

CROSS REFERENCE TO RELATED APPLICATION(S)

This application is a US national stage entry of PCT Application No. PCT/JP2017/027174 filed Jul. 27, 2017, which claims the benefit of the earlier filing date of JP Application No. JP 2016-162520 filed Aug. 23, 2016, both of which are incorporated by reference, in their entirety, for any purpose.

TECHNICAL FIELD

The present invention relates to a compound and a hydrogen supply method.

BACKGROUND ART

An organism (e.g. an animal) can allow, in its body, presence of active oxygen that can be produced in its body. Active oxygen is necessary for life support. For example, a method for promoting non-human animal/plant growth has been disclosed that includes applying, to plant or animal cells of either a seed or budding yeast, a plasma oxidation-reduction method of oxidizing or reducing amino acids by an active oxygen (such as a hydroxyl radical) species or active hydrogen in plasma (Patent document 1).

On the other hand, active oxygen is known to oxidize and damage cells that form a living body. For example, active oxygen, particularly a hydroxyl radical which has the strongest oxidizing power in active oxygen is possible causes various diseases such as skin disorders including skin aging and dermatitis of an animal. In addition, active oxygen can bring various disorders not only to an animal but also to a plant. Examples of the disorders brought about by active oxygen that can be generated in a plant include photosynthesis inhibition, leaf discoloration, and withering of a plant. Therefore, it is desirable that excess active oxygen, particularly the hydroxyl radical, which has not been used in a reaction useful for a living body, be prevented from being present in the body wherever possible.

Hydroxyl radicals in the body can be eliminated by reacting with some substances. Hydrogen is known as one example of the substances that eliminate hydroxyl radicals. It is water that is produced by hydrogen reacting with hydroxyl radicals, and hydrogen does not produce substances harmful to a living body. Thus, a device for producing hydrogen water containing hydrogen which eliminates hydroxyl radicals in the body has been proposed (e.g. Patent Document 2).

The concentration of hydrogen in the hydrogen water, however, is as low as 1.6 ppm (saturated hydrogen concentration) at a maximum. Further, hydrogen in the hydrogen water is easily diffused into air to remarkably reduce the concentration of hydrogen with elapse of time. Therefore, a method of ingesting hydrogen water does not make it easy to take in the body a sufficient amount of hydrogen for reacting with hydroxyl radicals in the body. Thus, for making it easy to take hydrogen in the body, a hydrogen-containing composition containing hydrogen and a surfactant has been proposed (Patent Document 3).

Meanwhile, the present inventors have researched decomposition of water and generation of hydrogen by silicon nanoparticles and the results of the research have been described (Non-Patent Document 1 and Patent Documents 4 and 5).

PRIOR ART DOCUMENTS

Patent Documents

Patent Document 1: Japanese Patent Laid-open Publication No. 2016-152796
Patent Document 2: Japanese Patent Publication No. 5514140
Patent Document 3: Japanese Patent Laid-open Publication No. 2015-113331
Patent Document 4: Japanese Patent Laid-open Publication No. 2016-155118
Patent Document 5: Japanese Patent Laid-open Publication No. 2017-104848

Non-Patent Document

Non-Patent Document 1: Shinsuke MATSUDA et al., Concentration of hydrogen molecules and splitting water using silicon nanoparticle, Extended Abstracts of the 62nd JSAP Spring Meeting, 2015, 11a-A27-6

SUMMARY OF THE INVENTION

Problems to be Solved by the Invention

However, even when high-concentration hydrogen water is ingested, the amount of hydrogen contained in 1 liter of the hydrogen water is only 18 ml at a maximum in terms of gas. In addition, depending on conditions, there is the problem of causing pneumophagia (so-called "burp") because a sufficient amount of hydrogen is not necessarily taken in the body. Therefore, limiting the means of taking hydrogen in the body to conventional "drinking water" makes it difficult to take a necessary amount of hydrogen in the body for sufficiently reducing active oxygen.

On the other hand, when a hydrogen-containing composition with hydrogen encapsulated by a surfactant is ingested, it is necessary to ingest a large amount of the hydrogen-containing composition for taking a sufficient amount of hydrogen in the body.

In addition, as described above, not only to an animal but also to a plant, excess active oxygen (typically hydroxyl radicals) which has not been used in a useful reaction can bring about various disorders (such as photosynthesis inhibition, leaf discoloration, and withering of a plant), so that such active oxygen in the body is required to be reduced wherever possible.

Solutions to the Problems

The present invention solves at least one of the above-described technical problems and can appropriately eliminate, remove, or reduced excess active oxygen (particularly hydroxyl radicals) in an animal to greatly contribute to health promotion and/or disease prevention of the animal. The present invention can also appropriately eliminate, remove, or reduce excess active oxygen (particularly hydroxyl radicals) in a plant to greatly contribute to prevention or suppression of photosynthesis inhibition, leaf discoloration, and/or a withering of a plant.

The present inventors have conducted earnest research and analyses on a material and a method that are capable of appropriately eliminating, removing, or reducing excess active oxygen (particularly hydroxyl radicals) in an animal and a plant. As a result, the present inventors have found that formation of an environment in which hydrogen is generated in a living body or is continuously generated in the vicinity of a living body (typically within 10 cm from the living body (more suitably within 1.5 cm)) leads to an increase in opportunity of bringing hydrogen into contact with active oxygen (particularly hydroxyl radicals) in the living body with higher accuracy.

As a result of repetitive earnest studies and analyses by the present inventors based on the above-described point of view, the present inventors have obtained very interesting knowledge. Specifically, the present inventors have found that certain characteristic silicon fine particles or aggregates thereof hardly generate hydrogen even when brought into contact with a water-containing liquid or a medium containing a water-containing liquid each having a pH value in a certain numerical range, but the silicon fine particles or the aggregates thereof are capable of remarkably generating hydrogen when brought into contact with a water-containing liquid or a medium containing a water-containing liquid each having a pH value in another numerical range (hereinafter, also referred to collectively as a "medium"). In addition, the present inventors have also obtained knowledge that the hydrogen generation amount considerably increases as the pH value increases. In the "water-containing liquid" in the present application includes in-vivo and ex-vivo water itself.

A hydrogen generation mechanism by a reaction of the silicon fine particles or the aggregates thereof with water molecules is represented by the following formula (Chemical Formula 1). As described above, however the present inventors have found that the reaction represented by the formula (Chemical Formula 1) is a limited reaction when the silicon fine particles or the aggregate thereof are brought into contact with a medium having a low pH value (typically a pH value of less than 5) but the reaction proceeds when the silicon fine particles or the aggregates thereof are brought into contact with a medium having a pH value of 6 or more. Therefore, it has been very interestingly clarified that even a water-containing liquid that is weakly acidic and has a pH value of 6 allows effective generation of hydrogen. The present inventors have found by further examination that in order to promote the generation of hydrogen, it is effective to bring the silicon fine particles or the aggregates thereof into contact with a medium having a pH value of more suitable 7 or more (or more than 7), further suitably more than 7.4 and with very suitably a medium that is basic (hereinafter, referred to as "alkaline") and has a pH value of more than 8.

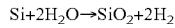  (Chemical Formula 1)

On the basis of the above-described knowledge, the present inventors have found that it is possible to solve at least a part of the above-described technical problems by utilizing the silicon fine particles or the aggregates thereof as well as appropriately adjusting or setting the usage environment of the silicon fine particles or the aggregates thereof. The present invention has been made on the basis of the above-described point of view.

One compound according to the present invention contains silicon fine particles having a capability of generating hydrogen or aggregates of the silicon fine particles.

The compound that contains the silicon fine particles or the aggregates thereof having a capability of generating hydrogen is capable of generating hydrogen in the body of, for example, an animal that has ingested the compound. When hydrogen is generated outside the body of an animal, the compound also allows the animal to dermally or transmucosally take hydrogen in its boy. As a result, it is possible to appropriately eliminate, remove, or reduce excessive active oxygen (particularly hydroxyl radicals) in its body and thus attain health promotion and/or disease prevention of the animal.

The ingestion method is not limited to oral ingestion. Also employable is allowing hydrogen to be taken in the body of an animal through its skin or mucous membrane. For example, when an animal has a bath using, for example, a puddle, the compound is disposed or charged into the puddle to generate hydrogen ($H_2$) in the puddle and thus bring the animal's skin or mucous membrane into contact with hydrogen.

For a plant, the compound can be disposed or charged into, for example, moisture (water-containing liquid) or fertilizer to be provided to the plant, to supply the plant with hydrogen generated from the compound. As a result, it is possible to appropriately eliminate, remove, or reduce excess active oxygen (particularly hydroxyl radicals) in the plant and thus attain prevention or suppression of photosynthesis inhibition, leaf discoloration, and/or withering of a plant.

From the above-described viewpoints, a suitable specific example is the compound blended in a medicine for an animal, a quasi-pharmaceutical product for an animal, food for a pet, healthy food for a pet, or feed for an animal, or the compound blended in a medicine for a plant, a quasi-pharmaceutical product for a plant, fertilizer for a plant, a growth promoter for a plant, or compost for a plant.

One production method for a compound according to the present invention is a production method for the above-described compound and includes a step of grinding silicon particles in an ethanol solution to form the silicon fine particles, and a hydrogen peroxide water treatment step of bringing the silicon fine particles or aggregates thereof into contact with hydrogen peroxide water.

The production method for a compound uses an ethanol solution and hydrogen peroxide water to be capable of producing a compound that is safer and more secure for a living body.

One hydrogen supply method according to the present invention includes a contact step of bringing, inside or outside a body of an animal, a compound that contains silicon fine particles having a capability of generating hydrogen or aggregates of the silicon fine particles into contact with a water-containing liquid having a pH value of 5 or more or a medium containing the water-containing liquid.

According to the hydrogen supply method, the silicon fine particles or the aggregates thereof having a capability of generating hydrogen are brought into contact with a water-containing liquid having a pH value in the above range or a medium containing the water-containing liquid inside or outside the body of an animal that ingests the silicon fine particles or the aggregates, to be capable of generating hydrogen inside or outside the body of the animal. As a result, hydrogen directly, or dermally or transmucosally taken in the body is capable of appropriately eliminating, removing, or reducing excess active oxygen (particularly hydroxyl radicals) in the body of an animal, so that it is possible to attain health promotion and/or disease prevention of the animal.

Another hydrogen supply method according to the present invention includes a contact step of bringing, inside or outside a body of a plant, a compound that contains silicon fine particles having a capability of generating hydrogen or aggregates of the silicon fine particles into contact with a water-containing liquid having a pH value of 5 or more or a medium containing the water-containing liquid.

According to the hydrogen supply method, the silicon fine particles or the aggregates thereof having a capability of generating hydrogen are brought into contact with a water-containing liquid having a pH value in the above range or a medium containing the water-containing liquid in the body of a plant or in the vicinity of the plant, to be capable of generating hydrogen inside or outside the body of the plant. As a result, hydrogen directly, or dermally or transmucosally taken in the body is capable of appropriately eliminating, removing, or reducing excess active oxygen (particularly hydroxyl radicals) in the body of the plant, so that it is possible to attain prevention or suppression of photosynthesis inhibition, leaf discoloration, and/or withering of a plant.

When a plant takes therein hydrogen generated from the silicon fine particles or the aggregates, the silicon fine particles or the aggregates can be disposed or charged into, for example, moisture (water-containing liquid) or fertilizer to be provided to the plant, to supply the plant with hydrogen (e.g. hydrogen dissolved in water) through, for example, a leaf, a stem, a cortex, and/or a root. As a result, it is possible to appropriately eliminate, remove, or reduce excess active oxygen (particularly hydroxyl radicals) in the body of the plant and thus attain prevention or suppression of photosynthesis inhibition, leaf discoloration, and/or withering of a plant. It is also possible to attain growth promotion or an increase in sugar content of, for example, a leaf vegetable, a strawberry, and a tomato.

Meanwhile, in the invention of the compound and in the invention of the hydrogen supply method, one preferred aspect is, for example, providing an impermeable film that covers the compound, or the silicon fine particles or the aggregates. For example, when removal or dissolution of at least a part of the film brings the compound, or the silicon fine particles or the aggregates into contact with a water-containing liquid having a pH value of 7 or more or a medium containing the water-containing liquid, it is possible to select a scene in need of generation of hydrogen with a high degree of freedom.

In the present application, the expression "crystallite" is employed rather than the expression "crystal grain (or crystal particle)" when the diameter of a crystal is in the "nm order." On the other hand, the expression "crystal grain (or crystal particle)" is employed when the diameter of a crystal is in the "μm order."

Here, the "silicon fine particles" in the present application include "silicon nanoparticles" having an average crystallite diameter in the nm order, specifically a crystallite diameter of 1 nm or more and 100 nm or less. In a narrower sense, the "silicon fine particles" in the present application include, as main particles, silicon nanoparticles having an average crystallite diameter at a nano level, specifically a crystallite diameter of 1 nm or more and 50 nm or less. Here, according to the present inventor, silicon nanoparticles having a main crystallite diameter of 1 nm or more and less than 10 nm are the "silicon fine particles" that attain the finest division as one employable aspect. In the present application, the silicon fine particles include not only individually dispersed silicon nanoparticles, but also silicon nanoparticles in a state of aggregates that are formed by natural gathering of a plurality of the silicon nanoparticles and have a size close to a μm size (generally 0.1 μm or more and 1 μm or less).

As described above, the "silicon fine particles" in the present application can be aggregated in a natural state to form aggregates having a diameter size at a μm level (e.g. about 1 μm). In the present application, a lump solid preparation that is obtained by artificially putting the silicon fine particles together through addition of a binding agent, compression, or the like and has such a size to be picked up by human fingers is sometimes referred to as a "solid formulation" for discriminating the lump solid preparation from the "aggregates." The "solid formulation" is one example of the "compound" in the present application. Typical examples of the "solid formulation" include tablets, and granules and a powdered preparation which assume a powdery form rather than a lump form. The "silicon fine particles" or the "aggregates thereof" in the present application are capable of forming a layer or a film (hereinafter, referred to collectively as a "layer").

Effects of the Invention

The one compound according to the present invention is capable of attaining health promotion and/or disease prevention of an animal. The compound is capable of attaining, for a plant, preventing or suppression of photosynthesis inhibition, leaf discoloration, and/or withering of a plant.

The one hydrogen supply method according to the present invention is capable of attaining health promotion and/or disease prevention of an animal. The other hydrogen supply method according to the present invention is capable of attaining prevention or suppression of photosynthesis inhibition, leaf discoloration, and/or withering of a plant.

BRIEF DESCRIPTION OF THE DRAWINGS

FIG. 1 shows photographs ((a) perspective view and (b) side view) of a solid formulation (compound) according to a first embodiment.

FIG. 2 shows a schematic diagram illustrating the relationship between the solid formulation (compound) according to the first embodiment contained in a medium (soil) and a plant (tree).

FIG. 3 shows a side view (a) illustrating a laminate structure of a layered solid formulation and a medium before generation of hydrogen in a modified example (2) of the first embodiment, and a side view (b) of the laminate structure of the layered solid formulation and the medium when hydrogen is generated in the modified example (2) of the first embodiment.

FIG. 3B shows a side view illustrating a structure of a layered solid formulation in a modified example (3) of the first embodiment.

FIG. 4 shows a graph illustrating the amount of hydrogen generated in Examples 1 and 2.

FIG. 5A shows a photograph illustrating a state of a solid formulation in accordance with the first embodiment directly after the solid formulation is brought into contact with pure water.

FIG. 5B shows a photograph illustrating a state of a solid formulation in accordance with the first embodiment about 60 seconds after the solid formulation is brought into contact with pure water.

FIG. 5C shows a photograph illustrating a state of a solid formulation in accordance with a modified example (6) of the first embodiment directly after the solid formulation is brought into contact with pure water.

FIG. 6 shows a graph illustrating the hydrogen generation amount in Examples 3 to 7.

FIG. 7 shows a graph (a) illustrating chronological changes in amount of dissolved hydrogen generated by bringing silicon fine particles prepared under each condition of a second embodiment into contact with an aqueous solution obtained by dissolving sodium hydrogencarbonate in pure water, and a graph (b) illustrating chronological changes in hydrogen generation amount per 1 g of the silicon fine particles of the second embodiment.

DESCRIPTION OF REFERENCE SIGNS

20: Base
70: Film
90a: Soil
90b: Medium
100: Solid formulation
100a: Layered solid formulation
200: Laminate structure

EMBODIMENTS OF THE INVENTION

Embodiments of the present invention will be described in detail with reference to the accompanying drawings.

First Embodiment

Silicon fine particles (or aggregates thereof) according to the present embodiment and a compound according to the present embodiment have a capability of generating hydrogen. The compound according to the present embodiment contains the aggregates or the silicon fine particles (typically having a crystallite diameter of 1 nm or more and 100 nm or less) having a capability of generating hydrogen. Hereinafter, silicon fine particles (or aggregates thereof) and a solid formulation (compound) containing the silicon fine particles (or the aggregates) will be described in detail as one example of the compound according to the present embodiment. In addition, a hydrogen supply method according to the present embodiment will be also described in detail.

[1] Silicon Fine Particles (or Aggregates Thereof) and Solid Formulation, and Production Method for Silicon Fine Particles (or Aggregates Thereof) and Solid Formulation The solid formulation according to the present embodiment is produced using silicon fine particles (hereinafter, also referred to as "silicon nanoparticles" for the sake of convenience) including, as main particles, silicon nanoparticles obtained by finely dividing, according to a bead mill method, a commercially available high-purity silicon particle powder (typically, manufactured by Kojundo Chemical Laboratory Co., Ltd., particle diameter distribution: <φ5 μm (but silicon particles having a crystal grain diameter of more than 1 μm, purity: 99.9% i-type silicon) as silicon particles. The present embodiment employs a step of grinding silicon particles in ethanol solution to form the silicon fine particles or aggregates of the silicon fine particles.

Specifically, 200 g of the high-purity silicon powder id dispersed in 4 L (liters) of a 99.5 wt % ethanol solution, φ0.5 μm zirconia beads (volume: 750 ml) are added, and the mixture is finely divided by performing grinding (one-step grinding) at a rotation speed of 2500 rpm for 4 hours using a bead mill apparatus (manufactured by AIMEX CO., Ltd. horizontal continuous ready mill, (model: RHM-08).

In the present embodiment, a separation slit provided in a grinding chamber of the bead mill apparatus separates the mixture into the beads and an ethanol solution containing silicon nanoparticles. The ethanol solution containing silicon nanoparticles that has been separated from the beads is heated to 30° C. to 35° C. with a vacuum evaporator. As a result, the ethanol solution is evaporated to give the silicon nanoparticles and/or aggregates thereof.

The silicon fine particles obtained by the above-mentioned method mainly include silicon nanoparticles having a crystallite diameter of 1 nm or more and 100 nm or less. More specifically, as a result of measuring the silicon nanoparticles by an X-ray diffractometer (SmartLab manufactured by Rigaku Corporation), the following values were obtained as one example. In a volume distribution, the mode diameter was 6.6 nm, the median diameter was 14.0 nm, and the average crystallite diameter was 20.3 nm.

The silicon nanoparticles were observed using a scanning electron microscope (SEM), and the result showed that the silicon nanoparticles were partially aggregated to form slightly large formless aggregates with about 0.5 μm or less. In addition, individual silicon nanoparticles were observed using a transmission electrode microscope (TEM), and the result showed that main silicon nanoparticles had a crystallite diameter of about 2 nm or more and 20 nm or less.

Thereafter, a first mixing step of mixing hydrogen peroxide water with the silicon nanoparticles in a glass container (hereinafter, also referred to as a "$H_2O_2$ treatment" or a "hydrogen peroxide water treatment step") is performed in the present embodiment. In the present embodiment, the temperature of the hydrogen peroxide water (3.5 wt % in the present embodiment) in the mixing step is 75° C. The mixing time is 30 minutes. Sufficient stir in the first mixing step (hydrogen peroxide water treatment step) is preferred to increase the opportunity of the silicon nanoparticles getting in contact with the hydrogen peroxide water. Even when the temperature of the hydrogen peroxide water in the first mixing step (hydrogen peroxide water treatment step) is, for example, about room temperature, at least a part of the effects of the present embodiment can be exhibited.

The silicon nanoparticles mixed with the hydrogen peroxide water are subjected to a solid-liquid separation treatment using a known centrifugal separator to remove the hydrogen peroxide water and thus give silicon nanoparticles. As a result, it is possible to obtain silicon nanoparticles having their surfaces treated with hydrogen peroxide water. Here, the treatment of the surfaces of the silicon nanoparticles with hydrogen peroxide water is capable of removing an alkyl group (e.g. a methyl group) present on the surfaces of the silicon nanoparticles. As a result, the silicon nanoparticles (and silicon file particles including, as main particles, the silicon nanoparticles) and aggregates thereof are capable of forming a state in which they have surfaces capable of getting direct contact with a medium capable of containing a water-containing liquid, while as a whole retaining hydrophilicity on their surfaces. Such a special surface treatment is capable of promoting the generation of hydrogen with higher accuracy.

Thereafter, a second mixing step of mixing the silicon nanoparticles with an ethanol solution is further performed in the present embodiment. Sufficient stir in the mixing step is preferred to increase the opportunity of the silicon nanoparticles getting in contact with the ethanol solution (99.5 wt % in the present embodiment). The silicon nanoparticles mixed with the ethanol solution are subjected to a solid-liquid separation treatment using a known centrifugal separator for removal of the ethanol solution that is highly volatile and then sufficiently dried to produce one type of final silicon nanoparticles according to the present invention.

In the present embodiment, as another type of final silicon nanoparticles, silicon nanoparticles were also produced, with the mixing time of the hydrogen peroxide water with the silicon nanoparticles set to 60 minutes in the first mixing step of the above-described steps. Another aspect of the present embodiment also includes appropriate control of the shape and the structure of the silicon fine particles and the aggregates thereof.

The present embodiment does not use an isopropyl alcohol solution unlike a second embodiment described later but uses the ethanol solution and the hydrogen peroxide water, and thus, it is worth noting that it is possible to provide a solid formulation (compound) capable of playing a role as a hydrogen supply material that is safer and more secure for a living body, a production method for the solid formulation (compound), and a hydrogen supply method.

The silicon nanoparticles in an amount of 5 mg are mixed with 495 mg of a sodium hydrogencarbonate powder (manufactured by Wako Pure Chemical Industries, Ltd., purity: 99.5%). The mixture is kneaded and formed into a substantially columnar lump body having a diameter of about 5 mm and a height of about 10 mm by a tableting method to give a solid formulation (compound) 100 shown in FIG. 1. FIG. 1(a) is a perspective view of the solid formulation (compound) 100 as one example, and FIG. 1(b) is a side view of the solid formulation (compound) 100 as the one example. One employable aspect is also an aspect in which the silicon fine particles (including aggregates thereof) not formed into a solid formulation (e.g. in a powder form) or aggregates of the silicon fine particles are contained in a "base material" such as a medicine for an animal, food for livestock or a pet, or feed for an animal, or a medicine for a plant, fertilizer for a plant, or compost for a plant, described later.

[2] Medium

Next, one employable aspect of the present embodiment is also preparing a "medium" with which the silicon nanoparticles (or the aggregates thereof) or the solid formulation (compound) 100 is brought into contact.

A material or a commercial product for the "medium" in the present embodiment is not particularly limited. One example of the medium is a water-containing liquid (including only water) present in the body of an animal. Another example of the medium is a medium that allows an animal (including a fish) or a plant to dermally or transmucosally take hydrogen in its body and is physiologically acceptable. Such a medium can allow at least a part of the effects of the present embodiment to be exhibited. One example of a site for taking hydrogen in the body is the skin itself or the mucous membrane itself for the case of an animal and a leaf, a stem, a cortex, or a root for the case of a plant.

A suitable example of the medium is at least one selected from the group consisting of a liquid form, a gel form, a cream form, a paste form, an emulsion form, and a mousse form, in terms of increasing the opportunity of a site of an animal or a plant getting contact with a water-containing liquid or a medium containing the water-containing liquid (hereinafter, also referred to collectively as a "medium"). Other suitable examples of the medium include soil containing rainwater or artificial water, an artificial shower that sprays water, an artificial pond, a puddle (including a naturally formed puddle), water in a preserve for farming fishes and shellfishes (including crustaceans; the same applies hereinafter) or seaweed, and water in an aquarium for fishes and shellfishes or seaweed. Therefore, in one example of the present embodiment, the production method for a medium is artificially producing the soil, the shower, the pond, or the puddle with use of known means. In any example, the medium is preferred to be alkaline in terms of promoting the generation of hydrogen.

As one example, the solid formulation (compound) 100 is as shown in FIG. 2, buried in soil (containing moisture) 90a in which a plant (tree) is planted or naturally grown, to utilize the soil 90a as the medium in the present embodiment. The solid formulation (compound) 100 is brought into contact with the soil 90a as the medium to generate hydrogen ($H_2$). As a result, it is possible for the tree in contact with the soil 90a to take hydrogen in its body through its root or cortex. As a result, it is possible to attain prevention or suppression of photosynthesis inhibition, leaf discoloration, growth promotion, and/or withering of a plant. Some plants are also capable of attaining an increase in sugar content. A typical example of the moisture in the present embodiment is rainwater or artificial water. The number or the amount of the solid formulation (compound) in the soil 90a is not particularly limited.

Although not shown in a drawing, another employable aspect of the present embodiment is also introducing or charging the solid formulation (compound) 100 into a naturally present or artificial puddle (medium) to bring the solid formulation (compound) 100 into contact with the water-containing liquid. The solid formulation (compound) 100 is brought into contact with the water-containing liquid to generate hydrogen ($H_2$). In this aspect, an animal gets contact with or is immersed in the puddle to be capable of taking hydrogen in its body through the water-containing liquid. As a result, hydrogen directly, or dermally or transmucosally taken in the body is capable of appropriately eliminating, removing, or reducing excess active oxygen (particularly hydroxyl radicals) in the body of the animal, so that it is possible to attain health promotion and/or disease prevention of the animal.

If the puddle has a pH value higher than weak activity (e.g. a pH value of 5 or more), the presence of sodium hydrogencarbonate containing the solid formulation (compound) 100 according to the present embodiment increases, as described later, the pH value to allow the puddle to satisfy the condition as the medium that allows easy generation of hydrogen ($H_2$). In other words, when the water-containing liquid such as a puddle is acidic, many solid formulations (compounds) 100 are required to be introduced or charged into the soil 90a to make the water-containing liquid satisfy the condition as the medium that allows easy generation of hydrogen ($H_2$).

The solid formulation (compound) 100 according to the present embodiment contains sodium hydrogencarbonate. Therefore, even when the soil 90a or the puddle as the medium is neutral or weakly acidic, the solid formulation (compound) 100 is buried, introduced, or charged into the soil 90a or the puddle as the medium to undergo a contact step of bringing the silicon fine particles or the aggregates thereof according to the present embodiment into contact with the medium. As a result, it is possible to change, for example, the soil 90a or the puddle to a weakly acidic medium having a pH value of 6 or more, more suitably a basic medium having a pH value of more than 7 and thus to promote the generation of hydrogen ($H_2$).

Therefore, it is possible to bring hydrogen ($H_2$) generated by the contact step into contact with the skin and/or the mucous membrane of an animal or with a leaf, a stem, a cortex, and/or a root of a plant through the soil 90a or the puddle as the medium. As a result, the present embodiment allows an animal or a plant to take hydrogen ($H_2$) in its body.

As described above, for example, the soil 90a or the puddle plays a role as the medium in the present embodiment. As a result, an animal is capable of taking hydrogen ($H_2$) in its body from its skin or mucous membrane through the medium or directly. A plant is capable of taking hydrogen ($H_2$) in its body from its leaf, stem, cortex, or root through the medium or directly.

In the present embodiment, the solid formulation (compound) 100, or the silicon fine particles (including the aggregates thereof) not formed into the solid formulation or the aggregates of the silicon fine particles are not limited to cases in which they are used as they are. One employable preferred aspect is also an aspect in which the solid formulation (compound) 100, or the silicon fine particles (including the aggregates thereof) not formed into the solid formulation or the aggregates of the silicon fine particles are contained in the "base material" such as a medicine for an animal, food for livestock or a pet, or feed for an animal, or a medicine for a plant, fertilizer for a plant, or compost for a plant. For example, one typical example is mixing or kneading as an additive, for example, 0.1 wt % to 50 wt % of the solid formulation 100, or the silicon fine particles (including the aggregates thereof) not formed into the solid formulation or the aggregates of the silicon fine particles, with the base material. Therefore, the "base material" is also the "compound" in a broad sense in the present invention as containing the solid formulation 100, or the silicon fine particles (including the aggregates thereof) not formed into the solid formulation or the aggregates of the silicon fine particles. Therefore, bringing such a base material into contact with the medium is employable as preferred means for allowing an animal or a plant to take hydrogen in its body, for example, dermally or transmucosally.

In addition, if the solid formulation (compound) according to the present embodiment does not contain sodium hydrogencarbonate, for example, the soil 90a or the puddles having a pH value of 5 or more is capable of satisfying the condition as the medium that allows easy generation of hydrogen ($H_2$). The pH value is more suitably 6 or more (or more than 6), further suitably 7 or more (or more than 7) in terms of attaining a medium that allows easy generation of hydrogen ($H_2$) with higher accuracy. The pH value is further suitably more than 7.4, very suitably more than 8).

Modified Example (1) of First Embodiment

In the compound and the hydrogen supply method according to the first embodiment, one preferred aspect is further including an introduction step of introducing a "pH adjusting agent" into the medium or the "base material," for adjusting the pH value of the soil 90a or the puddle in the first embodiment to make the soil or the puddle satisfy the condition for easier generation of hydrogen, in other words, to make the pH value of the soil or the puddle fall within the numerical range for easier generation of hydrogen.

The sodium hydrogencarbonate in the first embodiment is one example of the "pH adjusting agent," but the "pH adjusting agent" is not limited to sodium hydrogencarbonate. Therefore, the material for the "pH adjusting agent" is not limited as long as it is a material (hereinafter, also referred to as a "weak acidic agent") capable of adjusting the medium or the base material to weak acidity, or a pH value of 5 or more or 6 or more (or more than 6), or it is a material (hereinafter, also referred to as an "alkaline agent") capable of adjusting the medium or the base material to alkaline, or a pH value of more suitably 7 or more (or more than 7) (more suitably more than 7.4, further suitably more than 8). A typical example of the weak acidic agent is at least one acid or a salt thereof selected from the group consisting of citric acid, gluconic acid, phthalic acid, fumaric acid, and lactic acid. A typical example of the alkaline agent is at least one selected from the group consisting of potassium carbonate, sodium carbonate, sodium hydrogencarbonate, sodium hydroxide, and potassium hydroxide. The most suitable alkaline agent is sodium hydrogencarbonate in terms of physiology. This is because sodium hydrogencarbonate is widely used as a food additive and has a plurality of advantages such as a pH value adjustment function required in the present embodiment and excellent safety and versatility.

Modified Example (3) of First Embodiment

As another modified example of the first embodiment, the solid formulation (compound) according to the first embodiment can be formed in layers to form a laminate structure 200 of a layered solid formulation (compound) and a medium. FIG. 3A(a) shows a side view illustrating the laminate structure 200 of the layered solid formulation and the medium before generation of hydrogen, and FIG. 3A(b) shows a side view illustrating the laminate structure 200 of the layered solid formulation and the medium when hydrogen is generated.

As shown in FIGS. 3A(a) and 3A(b), the laminate structure 200 includes at least a layered solid formulation 100a and a medium 90b on or above a base 20 (e.g. fiber, a natural resin, a synthetic resin, metal, a semiconductor, ceramics, or glass). Here, as already described, a suitable example of the medium 90b is a material that is physiologically acceptable and is at least one selected from the group consisting of a liquid form, a gel form, a cream form, a paste form, an emulsion form, and a mousse form. The base 20 is not necessarily provided when the laminate structure 200 of the layered solid formulation and the medium can be held without particularly providing the base 20.

As shown in FIG. 3A(a), in a stage before generation of hydrogen, an impermeable film 70 is provided between the layered solid formulation (compound) 100a and the medium 90b so as not to allow the layered solid formulation (compound) 100a to get contact with the medium 90b. A film formed of a known impermeable material can be utilized as the film 70. For example, an example of the material for the impermeable film 70 is a polymer such as known polyethylene. As another example, one employable aspect is also employment of a water-disintegrable and impermeable sheet disclosed in International Publication No. WO 2011/036992.

On the other hand, as shown in FIG. 3A(b), drawing the film 70 in the arrow direction at least partially brings the layered solid formulation 100a into direct contact with the medium 90b. As a result, the layered solid formulation (compound) 100a can get contact with the medium 90b capable of containing a water-containing liquid having a pH value of 7 or more to generate hydrogen in cooperation with the pH adjusting agent typified by sodium hydrogencarbonate.

The present embodiment forms the structure so that drawing the film 70 in the arrow direction (toward the left on the paper) brings the layered solid formulation (compound) 100a into direct contact with the medium 90b. The method of removing the film 70, however, is not particularly limited. For example, one employable aspect is formation of the structure so that the medium 90b is brought into contact with the silicon fine particles (the layered solid formulation (compound) 100a in the present embodiment) or the aggregates thereof when at least a part of the film 70 is removed or dissolved. As regards an example of the material for dissolving at least a part of the film 70, one employable aspect is also employment of a water-disintegratable and impermeable sheet disclosed in International Publication No. WO 2011/036992. Another employable aspect is also covering with the impermeable film 70 the solid formulation (compound) 100 according to the first embodiment in place of the layered solid formulation (compound) 100a in a stage before generation of hydrogen. When removal or dissolution of the film 70 at least partially brings the solid formulation (compound) 100 into direct contact with the medium 90b, the same effects as those in the layered solid formulation (compound) 100a can be exhibited.

When the medium is, for example, at least one selected from the group consisting of a liquid form, a gel form, a cream form, a paste form, an emulsion form, and a mousse form, the two layers (the layered solid formulation (compound) 100a and the medium 90b) shown in FIG. 3A(b) are considered not to possibly retain a state of being clearly separated from each other. Such a case increases the contact area between the layered solid formulation (compound) 100a and the medium 90b and is thus rather preferred in terms of promoting the generation of hydrogen with higher accuracy.

Modified Example (3) of First Embodiment

As another modified example of the first embodiment, another employable aspect is also a layered solid formulation (compound) produced by forming the solid formulation (compound) according to the first embodiment in layers. A structure 200a as one example shown in FIG. 3B includes a layered solid formulation (compound) 100a on a base 20. The base 20 is not necessarily provided when the shape of the layered solid formulation (compound) can be held without particularly providing the base 20. The impermeable film 70 shown in the modified example (2) of the first embodiment may be provided so as to cover the layered solid formulation (compound) 100a, in terms of highly accurately avoiding contact with moisture in air.

As shown in FIG. 3B, one preferred aspect of the present embodiment is, for example, bringing the layered solid formulation (compound) 100a into contact with the animal skin or mucous membrane and then into contact with moisture-containing sweat or body fluid from the skin or mucous membrane to generate hydrogen. Such a case also allows an animal to take hydrogen in its body in the same manner as in the modified example (2) of the first embodiment. It is possible to supply, as the moisture, water (e.g. clean water) in place of the sweat or the body fluid by, for example, spraying before (e.g. directly before) using the layered solid formulation (compound) 100a.

It is worth noting that the structures of the laminate structures of the present embodiment are employable structures in various "scenes." For example, typical commercial products that can employ (possibly include) the medium are exemplified by the following items (1) to (3):

(1) one washing agent selected from the group consisting of shampoo for an animal and soap for an animal;

(2) one therapeutic material selected from the group consisting of ointment and fomentation; and (3) one hygienic material selected from the group consisting of a water-absorbent resin, water-absorbent nonwoven fabric, water-absorbent fiber, water-absorbent felt, and water-absorbent gel (or gelled agent).

Here, the "hygienic material" includes hygienic gloves, a head cover, a head band, a bed pad, a bed sheet, a clothing item, a wound treatment product (including a wound covering material, tape, and a bandage), a disposable diaper, gauze, a gown, a hygienic tissue (including a wet towel, a face washing towel, a patch, a wet tissue, and a napkin), absorbent cotton, a cotton swab, adhesive-plaster, and surgical tape.

Modified Example (4) of First Embodiment

As another modified example of the first embodiment, 4 g of citric acid (manufactured by Wako Pure Chemical Industries, Ltd., purity: 99.5%) is further added to 2 g of the silicon nanoparticles and 34 g of the sodium hydrogencarbonate powder that are used in the first embodiment, and the mixture is kneaded to form a substantially columnar lump body having a diameter of about 5 mm and a height of about 10 mm, so that the same solid formulation (compound) as the solid formulation (compound) 100 shown in FIG. 1 can be obtained.

Modified Example (5) of First Embodiment

As another modified example of the first embodiment, a solid formulation is obtained by the same treatments as in the modified example (4) of the first embodiment except that the amounts of the sodium hydrogencarbonate powder and citric acid are changed to 19 g and 19 g, respectively. This solid formulation (compound) is the same substantially columnar solid formulation (compound) as the solid formulation (compound) 100 shown in FIG. 1 and has a diameter of about 5 mm and a height of about 10 mm. The mixing ratio among citric acid, sodium hydrogencarbonate, and the silicon nanoparticles can be appropriately changed.

Modified Example (6) of First Embodiment

In the present embodiment, the same high-purity silicon particle powder as that used in the first embodiment (typically, silicon particles having a crystal grain diameter of more than 1 μm) is ground in one step by the procedures described in the first embodiment. In the present embodiment, the φ0.5 μm zirconia beads (volume: 750 ml) used in the one-step grinding are automatically separated from a solution containing silicon nanoparticles in a bead mill grinding chamber. Further φ0.3 μm zirconia beads (volume: 300 mml) are added to the solution containing silicon nanoparticles from which the beads have been separated, and the mixture is finely divided by performing grinding (two-step grinding) at a rotation speed of 2500 rpm for 4 hours.

The silicon nanoparticles including the beads are separated from the solution containing silicon nanoparticles as described above. The ethanol solution containing silicon nanoparticles that has been separated from the beads is heated to 40° C. using a vacuum evaporator in the same manner as in the first embodiment for solution evaporation of ethanol to give the silicon nanoparticles.

Modified Example (7) of First Embodiment

Another employable aspect is also further providing a physiologically acceptable covering layer that covers the solid formulation (compound) 100 according to the first embodiment or the solid formulations (compounds) described in the modified examples (4) and (5) of the first embodiment. For example, it is possible to employ a known coating agent (e.g. a known enteric material hardly soluble in the stomach) that covers the outermost layer of the solid formulation (compound) 100. An example of a physiologically acceptable covering layer applicable as a capsule preparation is a capsule which encapsulates the silicon fine particles (mainly the aggregates of the silicon fine particles) or the aggregates thereof and is produced from a known material (e.g. a known enteric material hardly soluble in the stomach). When the solid formulation (compound) 100 is employed, a disintegrating agent may be further included. For the disintegrating agent, a known material is employable. In addition, a preferred example of a more suitable disintegrating agent is an organic acid, and the most suitable example is citric acid. Here, the organic acid can also function as a binding agent that brings the silicon nanoparticles into a lump form.

The temperature condition is not particularly limited for the water-containing liquid for generating hydrogen or the medium capable of containing the water-containing liquid in the embodiments. The temperature of the medium that allows the generation of hydrogen, however, is higher than 0° C. and 50° C. or lower. The water-containing liquid or the medium having a temperature of suitable 20° C. (more suitably 25° C.) or higher and 50° C. or lower promotes the reaction of generating hydrogen. Further, the water-containing liquid or the medium having a temperature of 35° C. or higher and 50° C. or lower promotes the generation of hydrogen with higher accuracy. An upper limit of the temperature of the water-containing liquid or the medium is not particularly limited as long as an animal or a plant is not wound or damaged.

Hereinafter, the embodiments will be described in more detail by way of examples, but the embodiments are not limited to these examples.

Example 1

The present inventors checked the state of generation of hydrogen without performing a tableting step by a tableting method, to evaluate silicon nanoparticles themselves. Specifically, an experiment was conducted as Example 1, using silicon nanoparticles subjected to the one-step grinding in the first embodiment.

The silicon nanoparticles described in the first embodiment in an amount of 10 mg and in a form of a powdered preparation (i.e. the silicon nanoparticles were not either mixed or kneaded with a sodium hydrogencarbonate powder) were poured into a glass bottle having a volume of 100 ml (borosilicate glass having a thickness of about 1 mm, LABORAN Screw Tubular Bottle manufactured by AS ONE Corporation). Tap water having a pH value of 7.1 in an amount of 30 ml was poured into the glass bottle, the glass bottle was hermetically sealed under the temperature condition of a liquid temperature of 25° C., the concentration of hydrogen in the liquid in the glass bottle was measured, and the hydrogen generation amount was determined using the measured concentration of hydrogen. For measurement of the concentration of hydrogen, a portable dissolved hydrogen meter (Model: DH-35A manufactured by DKK-TOA CORPORATION) was used.

Example 2

Example 2 was conducted in the same manner as Example 1 except that 30 ml of tap water was poured and the temperature condition was changed to a liquid temperature of 37° C.

FIG. 4 shows the results of Examples 1 and 2. In FIG. 4, the absicca represents the time (min) during which the solid formulations (compound) was kept in contact with the water-containing liquid, and the ordinate of the graph represents the hydrogen generation amount.

As shown in FIG. 4, the generation of hydrogen was confirmed even when nearly neutral water was brought into contact with the silicon nanoparticles described in the first embodiment. It was clarified that a high liquid temperature increases the hydrogen generation amount. Particularly, it was confirmed that when the liquid temperature is 37° C. close to human body temperature, the generation of hydrogen is attained in a shorter time and a great amount (1.5 ml/g or more) of a hydrogen is continuously generated thereafter.

In addition to the results of Examples 1 and 2, the present inventors conducted the evaluations indicated in Example 3 and the following examples for the various solid formulations (compound) that were processed by a tableting method and are described in the first embodiment and the modified examples thereof.

Example 3

Employed as a sample for Example 3 was a solid formulation (compound) having one-fifth ($\varphi 10 \times 1.6$ mm, silicon nanoparticles: 16 mg, sodium hydrogencarbonate: 304 mg) the diameter and the height of one solid formulation (compound) 100 produced by the treatments described in the first embodiment.

The sample was placed in a stainless container having a volume of 60 ml. Pure water (pH value: 7.0) as an example of the water-containing liquid in an amount of 60 ml was poured into the stainless container to immerse the solid formulation (compound) in the pure water, and the liquid temperature was kept at 25° C. Under this condition, the glass bottle was hermetically sealed, the concentration of hydrogen in hydrogen water produced in the glass bottle was measured using the meter described in Example 1, and the hydrogen generation amount was determined.

The solid formulation (compound) gradually disintegrated its shape in the pure water with elapse of time. Sodium hydrogencarbonate was dissolved in the liquid with elapse of time after the solid formulation (compound) was brought into contact with the pure water, and the silicon nanoparticles were partially settled and left on the bottom of the container while almost uniformly diffused in the liquid. As a result, the solid formulation (compound) hardly retained its original shape and assumed a powdery form (or a fine powdery form; hereinafter, referred to collectively as a "powdery form") (hereinafter, a phenomenon in which the form of a solid formulation is disintegrated into a powdery form is referred to as "disintegration." Dissolution of a capsule of a capsule preparation encapsulating a powder also means that the form of a formulation is disintegrated, and exposure of a powder by dissolution of a capsule is also encompassed in "disintegration"). In this example, sodium hydrogencarbonate released with disintegration of the solid formulation (compound) was dissolved in water, and therefore the pH value of the water-containing liquid in the glass bottle increased to 8.3.

Example 4

Example 4 as a sample a solid formulation (compound) having one-fifth ($\varphi 10 \times 1.6$ mm, silicon nanoparticles: 16 mg, sodium by hydrogencarbonate: 272 mg, citric acid: 32 mg) the diameter and the height of the solid formulation (compound) produced by the treatments described as the modified example (4) of the first embodiment. The solid formulation (compound) was almost wholly disintegrated into a powdery form about 5 minutes after brought into contact with pure water under the temperature condition of a liquid temperature of 25° C. In the process of disintegration of the solid formulation (compound) (i.e. until 90 minutes after the solid formulation (compound) was brought into contact with pure water), sodium hydrogencarbonate and citric acid were released with disintegration of the solid formulation (compound), so that the water-containing liquid had a pH value of 7.6.

Example 5

Example 5 employed, as a sample, a solid formulation (compound) having one-fifth (φ10×1.6 mm, silicon nanoparticles: 16 mg, sodium hydrogencarbonate: 152 mg, citric acid: 152 mg) the diameter and the height of the solid formulation (compound) prepared by the procedures described as the modified example (5) of the first embodiment. The solid formulation (compound) was almost wholly disintegrated into a powdery form about 5 minutes after brought into contact with pure water under the temperature condition of a liquid temperature of 25° C. In the process of disintegration of the solid formulation (compound) (i.e. until 90 minutes after the solid formulation (compound) was brought into contact with pure water), sodium hydrogencarbonate and citric acid were released with disintegration of the solid formulation (compound), so that the water-containing liquid had a pH value of 6.0.

Example 6

Example 6 employed, as a sample, a solid formulation (compound) having one-fifth (φ10×1.6 mm, silicon nanoparticles: 16 mg, sodium hydrogencarbonate: 272 mg, citric acid: 32 mg) the diameter and the height of the solid formulation (compound) prepared by the procedures described as the modified example (6) of the first embodiment. The stainless container was held in a thermostatic bath to keep the liquid temperature at 37° C. As the water-containing liquid, pure water having a pH value of 7.0 was used. The solid formulation (compound) was almost wholly disintegrated into a powdery form about 5 minutes after brought into contact with pure water. Sodium hydrogencarbonate and citric acid were released with disintegration of the solid formulation (compound), so that the water-containing liquid had a pH value of 7.6.

Example 7

Example 7 as a sample a solid formulation (compound) having one-fifth (φ10×1.6 mm, silicon nanoparticles: 16 mg, sodium by hydrogencarbonate: 152 mg, citric acid: 152 mg) the diameter and the height of the solid formulation (compound) produced by the treatments described in the modified example (7) of the first embodiment. The stainless container was held in a thermostatic bath to keep the liquid temperature at 37° C. As the water-containing liquid, pure water having a pH value of 7.0 was used. The solid formulation (compound) was almost wholly disintegrated into a powdery form about 5 minutes after brought into contact with pure water. Sodium hydrogencarbonate and citric acid were released with disintegration of the solid formulation (compound), so that the water-containing liquid had a pH value of 6.0.

In the examples, it is possible to confirm by visual inspection how the solid formulation (compound) gradually disintegrates its shape in pure water with elapse of time. One example of how the solid formulation (compound) is disintegrated is shown by FIGS. 5A and 5B that are photographs illustrating how a solid formulation (compound) (an example in accordance with the first embodiment) formed using 2 g of the silicon nanoparticles and 38 g of sodium hydrogencarbonate behaves with elapse of time when charged into 500 ml of pure water. FIG. 5A illustrates the state of the solid formulation (compound) directly after the solid formulation (compound) was brought into contact with pure water. FIG. 5B illustrates the state of the solid formulation (compound) about 60 seconds after the solid formulation (compound) was brought into contact with pure water.

On the other hand, FIG. 5C shows a photograph illustrating the state of a solid formulation (compound) (an example in accordance with the modified example (6) of the first embodiment) formed using 2 g of the silicon nanoparticles, 19 g of sodium hydrogencarbonate, and 19 g of citric acid, directly after the solid formulation (compound) was brought into contact with pure water.

As shown by FIGS. 5A to 5C, it was confirmed that when the solid formulation (compound) was brought into contact with pure water, sodium hydrogencarbonate was dissolved in the liquid with elapse of time, and the silicon nanoparticles were partially settled and left on the bottom of the container while almost uniformly diffused in the liquid.

FIG. 6 shows the results of Examples 3 to 7. In FIG. 6, the abscissa represents the time (min) during which the solid formulation (compound) was kept in contact with the water-containing liquid, and the ordinate of the graph represents the hydrogen generation amount.

In Example 3, the solid formulation (compound) disintegrated its form to release sodium hydrogencarbonate as shown in FIGS. 5A and 5B. The hydrogen generation amount increased with elapse of contact time between the solid formulation (compound) and the water-containing liquid as shown in FIG. 6.

In comparison of Example 3 with Example 5 and comparison of Example 4 with Example 6, the hydrogen generation amount increased under a temperature condition of 37° C. close to human body temperature. Specifically, it is worth noting that Examples 3 and 6 were confirmed to be capable of generating 20 ml/g or more of hydrogen in 240 minutes (four hours).

Further, in comparison of the results of Examples 1, 2, and 6 in which the silicon nanoparticles retaining a powdery form were brought into contact with the water-containing liquid, with the results of Examples 3 to 5 and 7 in which the silicon nanoparticles were used as a solid formulation (compound), it was clarified that the silicon nanoparticles retaining a powdery form are capable of generating more hydrogen when brought into contact with the water-containing liquid, particularly until a certain time (e.g. one and a half hours) after the silicon nanoparticles are brought into contact with the water-containing liquid.

Experiment of Measuring Amount of Hydrogen Generated by Contact Between Silicon Nanoparticles and Medium>

The present inventors also checked chronological changes in amount of hydrogen generated by bringing the silicon fine particles (not the solid formulation (compound)) prepared under each condition of the present embodiment into contact with an aqueous solution obtained by dissolving sodium hydrogencarbonate in pure water.

Specifically, 11 mg of the silicon nanoparticles (first mixing step: 30 minutes) or 5 mg of the silicon nanoparticles (first mixing step: 60 minutes) are mixed in a glass container with an aqueous solution having sodium hydrogencarbonate (1.88 wt %) dissolved therein. The aqueous solution has a pH of about 8.3. Thereafter, the glass container was filled to its opening with the aqueous solution and covered with a lid so as not to allow entry of air for complete hermetic sealing.

The lid was made of polypropylene, but a multilayer filter of polyethylene and polypropylene was used as an inner lid to enable sufficient inhibition of transmission and leakage of generated hydrogen. Some time later after the hermetic sealing, the silicon fine particles prepared under each condition of the present embodiment are confirmed from their appearance and by visual inspection to have been evenly mixed in the whole aqueous solution.

FIG. 7(a) shows a graph illustrating chronological changes in concentration of dissolved hydrogen generated by bringing the silicon fine particles (not the solid formulation (compound)) prepared under each condition of the present embodiment into contact with an aqueous solution obtained by dissolving sodium hydrogencarbonate in pure water. FIG. 7(b) shows a graph illustrating chronological changes in hydrogen generation amount per 1 g of the silicon fine particles prepared under each condition. The graphs show for reference the results of using the silicon fine particles not subjected to the first mixing step. The amounts of dissolved hydrogen were measured using a portable dissolved hydrogen meter (manufactured by DKK-TOA CORPORATION, model: DH-35A).

As shown in FIGS. 7(a) and 7(b), it was clarified that the first mixing step promotes the generation of hydrogen. Particularly, as shown in FIG. 7(b), it is worth noting that the first mixing step is performed to continuously give a hydrogen generation amount of 40 ml or more in 2 hours after elapse of 2 hours from the start of generation of hydrogen.

Meanwhile, the hydrogen generation amount of the silicon fine particles subjected to the first mixing step with a mixing time of 60 minutes is considered to be smaller than the hydrogen generation amount of the silicon fine particles with a mixing time of 30 minutes due to the difference in thickness of an oxide film on the surfaces of the silicon fine particles. That is, it is considered that the silicon fine particles subjected to the first mixing step with a mixing time of 60 minutes had a thicker oxide film to make their direct contact with the medium (aqueous solution) difficult and thus to inhibit the generation of hydrogen.

According to further research and analyses by the present inventors, the silicon fine particles an attain sufficient surface areas capable of getting direct contact with the medium, while appropriately retaining hydrophilicity of the surfaces thereof, when subjected to the first mixing step with a mixing time of more than 2 minutes and 50 minutes or less (more suitably 3 minutes or more and 40 minutes or less, further suitably 4 minutes or more and 30 minutes or less, most suitably 5 minutes or more and 20 minutes or less). As a result, the generation of hydrogen can be more accurately promoted with the mixing time fallen within the above range.

Second Embodiment

Silicon fine particles (or aggregates thereof) according to the present embodiment and a compound according to the present embodiment have a capability of generating hydrogen as in the first embodiment. The compound according to the present embodiment contains silicon fine particles (or aggregates thereof) having a capability of generating hydrogen. The present embodiment is substantially the same as the first embodiment in regard to the compound and the hydrogen supply method except that an isopropyl alcohol (IPA) solution is employed in place of the ethanol solution employed in the first embodiment, so that duplicate description can be omitted.

[1] Silicon Fine Particles (or Aggregates Thereof) and Solid Formulation, And production Method for Silicon Fine Particles (or Aggregates Thereof) and Solid Formulation Hereinafter, silicon fine particles (or aggregates thereof) and a solid formulation (compound) containing the silicon fine particles (or the aggregates) will be described in detail as one example of the compound according to the present embodiment. In addition, a hydrogen supply method according to the present embodiment will be also described in detail.

For the solid formulation (compound) according to the present embodiment, silicon fine particles (hereinafter, also referred to as "silicon nanoparticles" for the sake of convenience) are used that include as main particles, silicon nanoparticles obtained by finely dividing according to a bead mill method, a commercially available high-purity silicon particle powder (typically, manufactured by Kojundo Chemical Co., Ltd., particle diameter distribution: <φ5 μm, purity: 99.9%, i-type silicon) as silicon particles.

Specifically, 15 g of a high-purity Si powder is dispersed in 300 ml of a 99% or more isopropyl alcohol (IPA) solution, φ0.5 μm zirconia beads (volume: 300 ml) are added, and the mixture is finely divided by performing grinding (one-step grinding) at a rotation speed of 2500 rpm for 4 hours using a bead mill apparatus (manufactured by AIMEX CO., Ltd.: RMB Batch-Type Ready Mill).

Using a stainless steel material filter (mesh: 0.35 mm) attached to a bead separation container (manufactured by AIMEX CO., Ltd.), the silicon nanoparticles including the beads are subjected to suction filtration to separate the beads from the silicon nanoparticles separated from the beads is heated to 30° C. to 35° C. using a vacuum evaporator, so that the isopropyl alcohol (IPA) solution is evaporated to give the silicon nanoparticles and/or aggregates thereof.

The silicon nanoparticles obtained by the above-mentioned method mainly include, as in the first embodiment, silicon nanoparticles having a crystallite diameter of 1 nm or more and 100 nm or less. Main silicon nanoparticles have a crystallite diameter of about 2 nm or more and 20 nm or less as in the first embodiment.

Specifically, 15 g of a high-purity Si powder is dispersed in 300 ml of a 99% or more isopropyl alcohol (IPA) solution, φ0.5 μm zirconia beads (volume: 300 ml) are added, and the mixture is finely divided by performing grinding (one-step grinding) at a rotation speed of 2500 rpm for 4 hours using a bead mill apparatus (manufactured by AIMEX CO., Ltd.: RMB Batch-Type Ready Mill).

Using a stainless steel material filter (mesh: 0.35 mm) attached to a bead separation container (manufactured by AIMEX CO., Ltd.), the silicon nanoparticles including the beads are subjected to suction filtration to separate the beads from the silicon nanoparticles. The IPA solution containing the silicon nanoparticles separated from the beads is heated to 40° C. using a vacuum evaporator, so that IPA is evaporated to give the silicon nanoparticles and/or aggregates thereof.

As in the first embodiment, the silicon nanoparticles obtained by the above-mentioned method include, as a main component, silicon nanoparticles mainly having a crystallite diameter of 1 nm or more and 100 nm or less. Main silicon nanoparticles have a crystallite diameter of about 2 nm or more and 20 nm or less as in the first embodiment.

In the same manner as in the first embodiment, the first mixing step of mixing hydrogen peroxide water with the silicon nanoparticles in a glass container is performed thereafter also in the present embodiment. The treatment of the surfaces of the silicon nanoparticles with hydrogen peroxide water is capable of forming silicon nanoparticles having a relatively thin and heterogeneous/incomplete oxide film on the surfaces thereof. As a result, the silicon nanoparticles (and silicon fine particles including, as main particles, the silicon nanoparticles) and/or aggregates thereof are capable of forming a state in which they have surfaces capable of getting direct contact with a medium capable of containing a water-containing liquid, while as a whole retaining hydrophilicity on their surfaces. Such a special surface treatment is capable of promoting the generation of hydrogen with higher accuracy.

Thereafter, the silicon nanoparticles possibly having the isopropyl alcohol (IPA) solution partially attached thereto are subjected to a solid-liquid separation treatment using a known centrifugal separator to remove the isopropyl alcohol (IPA) solution with high accuracy and then sufficiently dried to produce one type of final silicon nanoparticles according to the present embodiment.

In the present embodiment, as another type of final silicon nanoparticles, silicon nanoparticles were also produced, with the mixing time of the hydrogen peroxide water with the silicon nanoparticles set to 60 minutes in the first mixing step of the above-described steps.

The silicon nanoparticles can be, in the same manner as in the first embodiment, mixed with a sodium hydrogencarbonate powder to give a mixture, which is kneaded and then subjected to a tableting method to give a solid formulation.

Thereafter, the amount of hydrogen generated by contact between the silicon nanoparticles and the medium was examined to give the same results as the results of the first embodiment shown in FIG. 4.

Other Embodiments

One aspect of the production method for silicon fine particles in the compound includes a step of finely dividing silicon particles having a crystal grain diameter of more than 1 μm by a physical grinding method to form silicon fine particles mainly having a crystallite diameter of 1 nm or more and 100 nm or less. A suitable example of the physical grinding method is a method of grinding silicon particles by a beam mill grinding method, a planetary ball mill grinding method, a jet mill grinding method, or a combination of two or more thereof. However, in terms of production costs or ease of production control, a particularly suitable example is only a bead mill grinding method or a grinding method including at least a bead mill grinding method. The exemplified solid formulations (compounds) in the embodiments not only play a role as the hydrogen supply material but also play a role as a hydrogen generation material for a living body that enables safe generation of hydrogen in vivo or ex vivo (hydrogen supply material for a living body).

The embodiments employ, as a starting material, silicon particles i.e. a commercially available high-purity silicon particle powder. The starting material, however, is not limited to such silicon particles. One preferred aspect is also employing, as the starting material, for example, silicon chips, silicon cutting scraps, or silicon polishing scraps (hereinafter, also referred to as "silicon chips etc." or "chips etc.") which are usually disposed of as wastes in cutting processing of silicon in a process for production of a silicon wafer to be used in semiconductor products such as a solar cell, in terms of attaining lower cost and/or giving finer silicon nanoparticles. The object of the "silicon fine particles" is not limited to crystalline silicon. For example, it is also possible to use, as the starting material in the embodiments, silicon particles obtained by finely dividing an amorphous silicon layer formed on a known substrate by a CVD method. It is also possible to use, as the starting material or the finally-formed silicon fine particles in the embodiments, amorphous or crystalline silicon particles somewhat directly produced by, for example, a CVD method, a laser method, or an arc-discharge method.

The disclosure of the embodiments or the examples is intended for describing the embodiments and is not intended for limiting the present invention. In addition, modified examples within the scope of the present invention, including other combinations of the embodiments and the examples, are also to be included in the scope of claims.

INDUSTRIAL APPLICABILITY

A compound and a hydrogen supply method according to the present invention can be widely use din agriculture, agriculture and stock raising forestry, fishery, a pet industry, industries of bonsai plants and flower arrangement, or medical industries including a veterinary industry and a tree doctor industry.

What is claimed is:

1. A medicine for an animal or a human or a feed for a livestock or food for a pet comprising a solid formulation, the solid formulation comprising silicon fine particles having a capability of generating hydrogen or aggregates of the silicon fine particles,
   wherein the silicon fine particles or the aggregates of the silicon fine particles have surfaces capable of getting direct contact with water of a water-containing medium while retaining hydrophilicity on the surfaces, wherein the silicon fine particles or the aggregates of the silicon fine particles have a heterogeneous or incomplete oxide film on the surfaces, and wherein the silicon fine particles or the aggregates are blended into the solid formulation.

2. The medicine for the animal or the human or the feed for the livestock or the food for the pet comprising the solid formulation according to claim 1, wherein the silicon fine particles include silicon fine particles having a crystallite diameter of 1 nm or more and 100 nm or less.

3. The medicine for the animal or the human or the feed for the livestock or the food for the pet comprising the solid formulation according to claim 1, further comprising a pH adjusting agent being capable of making the water-containing medium have a pH value of 5 or more, wherein the water-containing medium is in contact with the silicon fine particles or the aggregates.

4. The medicine for the animal or the human or the feed for the livestock or the food for the pet comprising the solid formulation according to claim 3, wherein the pH adjusting agent is at least one selected from the group consisting of potassium carbonate, sodium carbonate, sodium hydrogencarbonate, sodium hydroxide, and potassium hydroxide.

5. The medicine for the animal or the human or the feed for the livestock or the food for the pet comprising the solid formulation according to claim 3, wherein the medium is at least one selected from the group consisting of a liquid form, a gel form,
   a cream form, a paste form, an emulsion form, and a mousse form.

6. A hydrogen supply method comprising contacting the medicine for the animal or the human or the feed for the livestock or the food for the pet comprising the solid formulation according to claim 1 with the water-containing medium having a pH value of 5 or more, inside or outside of the body of the animal or the human.

7. The hydrogen supply method according to claim 6, wherein
the silicon fine particles include silicon fine particles having a crystallite diameter of 1 nm or more and 100 nm or less.

8. The hydrogen supply method according to claim 6, wherein the water-containing medium has a pH value of 6 or more.

9. The medicine for the animal or the human or the feed for the livestock or the food for the pet comprising the solid formulation according to claim 1, wherein the water-containing medium includes in-vivo or ex-vivo water.

10. A medicine, a fertilizer, or a compost for a plant comprising a solid formulation, the solid formulation comprising silicon fine particles having a capability of generating hydrogen or aggregates of the silicon fine particles,
wherein the silicon fine particles or the aggregates of the silicon fine particles have surfaces capable of getting direct contact with water of a water-containing medium while retaining hydrophilicity on the surfaces,
wherein the silicon fine particles or the aggregates of the silicon fine particles have a heterogeneous or incomplete oxide film on the surfaces, and
wherein the silicon fine particles or the aggregates are blended into the solid formulation.

11. The medicine, the fertilizer, or the compost for the plant comprising the solid formulation of claim 10, wherein the water-containing medium includes in-vivo or ex-vivo water.

12. The medicine, the fertilizer, or the compost for the plant comprising the solid formulation of claim 10, further comprising a pH adjusting agent being capable of making the water-containing medium have a pH value of 5 or more, wherein the water-containing medium is in contact with the silicon fine particles or the aggregates.

13. A hydrogen supply method comprising:
contacting the medicine, the fertilizer, or the compost for the plant comprising the solid formulation according to claim 10 with the water-containing medium having a pH value of 5 or more.

* * * * *